United States Patent [19]

Nakagawa et al.

[11] Patent Number: 5,260,064
[45] Date of Patent: Nov. 9, 1993

[54] PERCUTANEOUS-ADMINISTRATION-TYPE PHARMACEUTICAL PREPARATION OF NITROGLYCERIN

[75] Inventors: Takashi Nakagawa, Ohtsu; Hiroko Tsukahara, Takatsuki; Masayasu Kurono, Mie; Makoto Sato, Aichi; Tsutomu Ishida, Iwakura; Kazushi Tokita, Aichi; Mitsuji Nakano, Nagoya, all of Japan

[73] Assignees: Sekisui Kagaku Kogyo Kabushiki Kaisha, Osaka; Sanwa Kagaku Kenkyusho Co., Ltd., Nagoya; Nippon Oil & Fats Co., Ltd., Tokyo, all of Japan

[21] Appl. No.: 680,723

[22] Filed: Apr. 4, 1991

[30] Foreign Application Priority Data

Apr. 6, 1990 [JP] Japan ................................ 2-92694

[51] Int. Cl.$^5$ .............................................. A61F 13/02
[52] U.S. Cl. .................................. 424/448; 424/449; 424/443; 424/447
[58] Field of Search ................ 424/448, 449, 447

[56] References Cited

U.S. PATENT DOCUMENTS

| 4,685,911 | 8/1987 | Kono et al. ................ 424/448 |
| 4,751,087 | 6/1988 | Wick ............................ 424/449 |
| 4,971,799 | 11/1990 | Nakagawa et al. ........ 424/448 |

FOREIGN PATENT DOCUMENTS

| 0156080 | 10/1985 | European Pat. Off. |
| 54-16566 | 6/1979 | Japan . |
| 55-2604 | 1/1980 | Japan . |
| 55-94316 | 7/1980 | Japan . |
| 56-125311 | 10/1981 | Japan . |
| 56-133381 | 10/1981 | Japan . |
| 57-14522 | 1/1982 | Japan . |
| 57-59806 | 4/1982 | Japan . |
| 57-77617 | 5/1982 | Japan . |
| 57-500831 | 5/1982 | Japan . |
| 61-502760 | 11/1986 | Japan . |
| 62-502965 | 11/1987 | Japan . |
| 63-246325 | 10/1988 | Japan . |
| 59-207149 | 11/1988 | Japan . |

Primary Examiner—Thurman K. Page
Assistant Examiner—Leon R. Horne
Attorney, Agent, or Firm—Nikaido, Marmelstein, Murray & Oram

[57] ABSTRACT

A percutaneous-administration-type pharmaceutical preparation of nitroglycerin is provided. The preparation comprises a backing that is impervious to medicines, and a pressure-sensitive adhesive layer that is placed on one surface of said backing, wherein said pressure-sensitive adhesive layer contains an alkyl (meth)acrylate (co)polymer in the concentration of 35-85% by weight, nitroglycerin in the concentration of 10-30% by weight, and a silicic acid anhydride in the concentration of 5-20% by weight, said (co)polymer contains as major (co)polymer components alkyl (meth)acrylates with alkyl groups having 6 or more carbon atoms, which alkyl (meth)acrylates include 2-ethylhexyl methacrylate in the concentration of 40-100% by weight based on the total weight of said alkyl (meth)acrylates. The preparation makes it possible for nitroglycerin to be absorbed percutaneously at a controlled rate for a long period of time. Also, even a compact preparation can supply a sufficient amount of nitroglycerin. Moreover, the preparation can be manufactured at low cost without any complicated process.

5 Claims, No Drawings

PERCUTANEOUS-ADMINISTRATION-TYPE PHARMACEUTICAL PREPARATION OF NITROGLYCERIN

BACKGROUND OF THE INVENTION

1. Field of the Invention

This invention relates to a pharmaceutical preparation in pressure-sensitive adhesive tape form that permits the percutaneous absorption of nitroglycerin over a long period of time at a controlled rate.

2. Description of the Prior Art

Nitroglycerin is used as a medicine for the treatment and for the prevention of heart disease such as angina pectoris, myocardial infarction, cardiac insufficiency, and the like. When nitroglycerin is administered by, for example, intravenous injection, its effects are lost after a very short period of time. Also, because the nitroglycerin in the blood is thereby raised to a high level for a short period of time, there are the disadvantages of side effects such as headache, dizziness, orthostatic hypotension, etc. In order to keep the blood level of nitroglycerin at a fixed value for relatively long periods of time, a preparation that has a layer of adhesive that contains nitroglycerin on a backing can be used, and the nitroglycerin can be absorbed percutaneously. The drug nitroglycerin is relatively easily absorbed through the skin. For that reason, if adhesives such as natural rubber, polyisobutyrene, silicone resin, etc., in which nitroglycerin is relatively insoluble are used, the skin-adhesive partition coefficient of nitroglycerin is high, and the permeation rate through the skin is therefore too high, resulting in the side effects mentioned above. In order to achieve the effective use of the pharmacological effects of nitroglycerin, continuous percutaneous absorption by which a blood level of nitroglycerin of 0.05–2.0 ng/ml is maintained is preferable. For this purpose, a number of steps have been taken, such as the selection of an adhesive base by which the rate of percutaneous absorption of the nitroglycerin can be controlled.

Preparations of nitroglycerin comprising adhesive bases that can control the release of nitroglycerin more readily than those mentioned above have been disclosed in, for example, Japanese Laid-Open Patent Publications 56-133381, 57-77617, 55-2604, and 63-246325 which corresponds to U.S. Pat. No. 4,971,799. For example, Japanese Laid-Open Patent Publication 57-77617 discloses a preparation containing a copolymer as an adhesive base that can be obtained by the copolymerization of dodecyl methacrylate, a functional monomer such as acrylic acid, and a specific alkyl (meth)acrylate, and the like. The preparation of nitroglycerin is prepared by dissolving the adhesive base into an appropriate organic solvent, coating the resulting solution on a backing to form an adhesive layer, and then drying the adhesive layer. However, because a large amount of monomers that can form a relatively softer copolymer, e.g., dodecyl methacrylate, are used in the copolymerization process, the resulting copolymer does not have sufficient cohesive strength. For that reason, it is difficult to add nitroglycerin to the adhesive layer in high concentrations. In order to administer a fixed amount of nitroglycerin, it is necessary to use a large surface area of the preparation, which makes a patient uncomfortable due to irritation.

Japanese Laid-Open Patent Publication 63-246325 which corresponds to U.S. Pat. No. 4,971,799 discloses preparations of nitroglycerin containing as an adhesive base a copolymer of specific alkyl (meth)acrylates in an adhesive layer. The number of carbons in the alkyl groups of the alkyl (meth)acrylate is 6 or more. The copolymer contains 2-ethylhexyl methacrylate as a copolymer component in the concentration of 40–90% by weight, and has a rolling ball tack value of 2 or less. The adhesive layer can contain nitroglycerin in relatively high concentrations. However, when a large amount of nitroglycerin is contained in the adhesive layer, the adhesive layer will soften, and consequently, adhesiveness to the surface of the skin is not sufficient. In other words, a preparation with sufficient adhesiveness of this type of preparation cannot release a sufficient amount of nitroglycerin.

Moreover, preparations of nitroglycerin which is produced by the impregnation method are known. In this method, first, an adhesive layer that does not contain any drug is formed on a backing, and a soft ointment or the like containing nitroglycerin is applied to this adhesive layer and left to mature so that nitroglycerin is transferred to the adhesive layer. However, in this impregnation method, it is difficult to obtain an adhesive base in which the nitroglycerin is distributed uniformly at a high concentration. In this way, the preparation that is obtained by the impregnation method has a small amount of nitroglycerin in the adhesive base, so that long pharmacological term effectiveness is not achieved. Moreover, the amount of nitroglycerin per unit of surface area is small, and it is necessary to use a large surface area of the preparation in order to administer a suffient amount of nitroglycerin.

Japanese National Publications 61-502760 and 62-502965 disclose preparations containing nitroglycerin in high concentrations (about 20 to 60% by weight) in acrylic-type adhesive bases to improve the rate of release of the nitroglycerin. However, the presence of nitroglycerin in high concentrations in the adhesive base of these preparations may be in danger of explosion. Also, in order that a large amount of nitroglycerin can be contained in the adhesive base, polar groups are introduced into the adhesive base polymer, or the adhesive base polymer is crosslinked so that the cohesive strength of the adhesive base is improved. However, the following problems arise. For example, the adhesive base polymer is crosslinked by a chemical reaction after the addition of nitroglycerin in Japanese National Publication 61-502760 mentioned above. The crosslinking reaction causes the nitroglycerin to decompose, resulting in the accumulation of the decomposed products. Also, it is difficult to complete the crosslinking reaction described above, and the unreacted active groups will remain in the adhesive base. These decomposed products and unreacted active groups may irritate the skin. Moreover, there is another problem that when the adhesive base is treated as described above to improve its cohesive strength, the release of the nitroglycerin will be reduced. To solve this problem, auxiliary absorbents are used to increase the release of nitroglycerin in Japanese National Publication 62-502965 mentioned above. However, because the auxiliary absorbents with interfacial activity generally irritate the skin, they are not preferred for use as a component of the preparation.

Additionally, preparations that can control the percutaneous absorption of nitroglycerin in other manners than the selection of an adhesive base have been proposed. For example, Japanese Patent Publication 54-16566 discloses a preparation of nitroglycerin obtained by forming a storage layer containing nitroglycerin in a high concentration on a backing, and then layering a membrane with micro-pores, for a controlled release and an adhesive layer in this order thereon. Japanese Laid-Open Patent Publications 55-94316, 57-14522, and 57-59806, and Japanese National Publication 57-500831 disclose preparations composed of two layers, a base layer of non-adhesive resin such as polyvinyl alcohol containing nitroglycerin therein, and an adhesive layer disposed on the base layer, by which the base layer is allowed to adhere to the skin surface. Japanese Laid-Open Patent Publication 59-207149 and 56-125311 disclose preparations obtained by layering two or more base layers containing different concentrations of nitroglycerin on a backing, and then layering an adhesive layer thereon. Also, a preparation that has an adhesive layer containing microencapsulated nitroglycerin particles that were obtained by encapsulating nitroglycerin particles by a micro-pore film has been proposed. However, the manufacture of all of these preparations is complicated, which makes it difficult in to obtain a preparation that contains nitroglycerin at low cost.

SUMMARY OF THE INVENTION

The percutaneous-administration-type pharmaceutical preparation of nitroglycerin of this invention, which overcomes the above-discussed and numerous other disadvantages and deficiencies of the prior art, comprises a backing that is impervious to medicines, and a pressure-sensitive adhesive layer that is placed on one surface of said backing, wherein said pressure-sensitive adhesive layer contains an alkyl (meth)acrylate (co)polymer in the concentration of 35-85% by weight, nitroglycerin in the concentration of 10-30% by weight, and a silicic acid anhydride in the concentration of 5-20% by weight, said (co)polymer contains as major (co)polymer components alkyl (meth)acrylates with alkyl groups having 6 or more carbon atoms, which alkyl (meth)acrylates include 2-ethylhexyl methacrylate in the concentration of 40-100% by weight based on the total weight of said alkyl (meth)acrylates.

The method for the manufacture of percutaneous-administration-type pharmaceutical preparations of nitroglycerin of this invention comprises: applying an organic-solvent solution that contains an alkyl (meth)acrylate (co)polymer, nitroglycerin, and a silicic acid anhydride to one surface of a backing that is impervious to medicines; and drying said coated layer on the backing, resulting in a pressure-sensitive adhesive layer, wherein said (co)polymer contains as major (co)polymer components alkyl (meth)acrylates with alkyl groups having 6 or more carbon atoms, which alkyl (meth)acrylates include 2-ethylhexyl methacrylate in the concentration of 40-100% by weight based on the total weight of said alkyl (meth)acrylates, said organic solvent has a solubility parameter of 8.9-9.9, and said pressure-sensitive adhesive layer contains said (co)polymer in the concentration of 35-85% by weight, said nitroglycerin in the concentration of 10-30% by weight, and said silicic acid anhydride in the concentration of 5-20% by weight.

In a preferred embodiment, the copolymer contains as a major copolymer component 2-ethylhexyl methacrylate in the concentration of 40 to 90% by weight based on the total weight of said alkyl (meth)acrylates.

In a preferred embodiment, the (co)polymer has a rolling ball tack value of 2 or less.

In a preferred embodiment, the pressure-sensitive adhesive layer contains an alkyl ester of fatty acid in the concentration of 25% by weight or less.

In a preferred embodiment, the silicic acid anhydride comprises 20-80% by weight of a hydrophobic silicic acid anhydride, and 80-20% by weight of a hydrophilic silicic acid anhydride.

Thus, the invention disclosed herein makes possible the objectives of: (1) providing a percutaneous-administration-type pharmaceutical preparation of nitroglycerin with which the level of nitroglycerin in the blood can be maintained at a fixed level for, a long period of time for example, 24 hours or more, at a controlled rate of absorption; (2) providing a compact percutaneous-administration-type pharmaceutical preparation of nitroglycerin with a simple structure having less skin irritation; and (3) providing a method for the manufacture of the above-mentioned preparation with simple processes.

DESCRIPTION OF THE PREFERRED EMBODIMENTS

In the percutaneous-administration-type pharmaceutical preparation of nitroglycerin of this invention, an alkyl (meth)acrylate (co)polymer that does not contain any polar group is used as an adhesive base material. Alkyl (meth)acrylates which are the (co)polymerization ingredients of this alkyl (meth)acrylate (co)polymer, have alkyl groups with 6 or more carbon atoms. As this kind of alkyl (meth)acrylate, there are 2-ethylhexyl (meth)acrylate, hexyl (meth)acrylate, heptyl (meth)acrylate, octyl (meth)acrylate, dodecyl (meth)acrylate, stearyl (meth)acrylate, etc. (Co)polymer made from these kinds of alkyl (meth)acrylate is saturated by about 35% by weight or less of nitroglycerin. If the carbon number of the alkyl groups mentioned above is less than 6, the affinity of this kind of (co)polymer for nitroglycerin is very high. Then, the skin-adhesive partition coefficient of nitroglycerin becomes small, and the percutaneous absorption of nitroglycerin is reduced.

Moreover, 40-100% by weight, preferably 40-90% by weight, and more preferably, 60-80% by weight of the alkyl (meth)acrylate that forms the (co)polymer, is 2-ethylhexyl methacrylate. In this way, when the (co)polymer contains the alkyl (meth)acrylate having an alkyl group of 6 or more carbon atoms, and 2-ethylhexyl methacrylate in the range mentioned above, it is saturated by about 10-30% by weight of nitroglycerin. When nitroglycerin is mixed with this kind of (co)polymer, the (co)polymer will have a suitable degree of polarity. Also, because the affinity of nitroglycerin to the copolymer is suitable, the nitroglycerin can be absorbed percutaneously at a fixed rate over a long period of time. If the amount of 2-ethylhexyl methacrylate in the (co)polymer is less than 40% by weight, and nitroglycerin is added to the copolymer in a high concentration, the pressure-sensitive adhesive layer will soften excessively due to the reduction of its cohesive strength. For that reason, when the preparation is peeled from the skin surface, the adhesive material will remain on the skin surface. Since the adhesive strength of such a (co)polymer is great, the removal of the preparation causes pain. When the amount of 2-ethylhexyl methacrylate in the copolymer is more than 90% by weight, a relatively hard pressure-sensitive adhesive layer is obtained, and the adhesive strength of the preparation is slightly decreased. The release of nitroglycerin from such a preparation is also slightly decreased. Other monomers than 2-ethylhexyl methacrylate are chosen so that the copolymer from these monomers will preferably have a rolling ball tack value of 2 or less.

The (co)polymer that can be used in this invention has preferably a rolling ball tack value of 2 or less. If the rolling ball tack value of the (co)polymer is more than 2, the adhesive material is liable to remain on the skin surface when the resulting preparation is peeled from the skin.

The rolling ball tack value is measured according to the procedure of JIS Z0237, Test Procedures for Adhesive Tape, and Adhesive Sheet, by the use of an adhesive tape sample having a (co)polymer layer with about 50–100 μm thickness.

When needed, a trace amount of radical polymerizable multi-functional monomer may be included as a copolymer component in the (co)polymer mentioned above. This multi-functional monomer has two or more radical polymerizable groups such as a vinyl group, allyl group, etc., per molecule of the monomer. For example, there are divinylbenzene, methylene bis-acrylamide, ethylene glycol di(meth)acrylate, propylene glycol di(meth)acrylate, butylene glycol di(meth)acrylate, hexylene glycol di(meth)acrylate, polyethylene glycol di(meth)acrylate, polypropylene glycol di(meth)acrylate, trimethylolpropane tri(meth)acrylate, and the like. When these multi-functional monomers are added at the time of (co)polymerization, a copolymer having higher polymerization degree can be obtained, so the resulting adhesive material will have excellent cohesion. Therefore, when the pharmaceutical preparation of nitroglycerin is removed from the skin, the adhesive material will not remain on the skin surface. The multi-functional monomers are added in a concentration of 0.1% by weight or less of the total monomers that form the (co)polymer, and ordinarily 0.01–0.1% by weight. If more than 0.1% by weight of the multi-functional monomers are used, a uniform polymer solution cannot be obtained because of the gelation at the time of the polymerization.

The (co)polymer can be prepared by the solution-polymerization (radical polymerization) technique or the like. For example, two or more kinds of alkyl (meth)acrylates including 2-ethylhexyl methacrylate mentioned above, and a multi-functional monomer as needed are charged into a reaction vessel together with a solvent, and allowed to polymerize under a nitrogen atmosphere at 60°–100° C. while being agitated with a peroxide, etc. as a catalyst. The copolymer obtained in this way is not in itself adhesive. However, when nitroglycerin is added to this (co)polymer, the plasticization effect of the nitroglycerin causes the development of an appropriate degree of adhesiveness. The (co)polymer mentioned above is contained in the adhesive layer in an amount of 35–85% by weight, preferably 45–75% by weight, more preferably 50–65% by weight for the total weight of the adhesive layer.

In the pressure-sensitive adhesive layer of the preparation of nitroglycerin of this invention, a silicic acid anhydride is contained to improve the cohesive strength of the adhesive layer. The amount of the silicic acid, depending on the amount of nitroglycerin and the composition of the adhesive material, is usually 5–20% by weight, and preferably 8–18% by weight for the total weight of the pressure-sensitive adhesive layer. If the amount of the silicic acid anhydride is less than 5% by weight, the cohesive strength of the pressure-sensitive adhesive layer will not be improved, significantly. On the other hand, if more than 20% by weight of the silicic acid anhydride is added, the pressure-sensitive adhesive layer will lose its adhesiveness. A fine powdered silicic acid anhydride (consisting of silic oxides) having a particle size of about 0.005 to about 100 μm can preferably be used.

The silicic acid anhydride includes a hydrophilic silicic acid anhydride, and a hydrophobic silicic acid anhydride. The hydrophilic silicic acid anhydride has hydroxyl groups on its surface. The hydrophobic silicic acid anhydride has hydroxyl groups on its surface, and about 50% or more of the hydroxyl group are modified, so that the silicic acid has substantial hydrophobic properties. The hydrophilic silicic acid anhydride to be used is usually fine primary particles having a particle size of 0.005 to 0.1 μm which is prepared by the gaseous phase or liquid phase technique. A porous silica gel (particle size: about 1 to 100 μm) obtained by binding these primary particles through a siloxane linkage three-dimensionally is also used as the silicic acid anhydride. The fine primary particles prepared by the gaseous phase or liquid phase technique include, for example, Aerosil 130, Aerosil 200, Aerosil 300, Aerosil 380 (all manufactured by Nippon Aerosil Co., Ltd.), and the like. The porous silica gel particle includes, for example, SYLOID (manufacture by FUJI-DAVISON CHEMICAL Co., Ltd.). The hydrophobic silicic acid anhydride includes, for example, silica particles, the surface of which is coated with dimethyl silanol groups by treating the surface of the particles of the hydrophilic silicic acid anhydride with dimethyl dichlorosilane. Also, hydrophobic silica particles obtained by subjecting the hydrophilic silicic acid anhydride particles to octylsilylation or trimethylsilylation, or by treating the surface of the hydrophilic silicic acid anhydride with silicone oil to make them hydrophobic are also used. The hydrophobic silicic acid anhydride includes for example Aerosil R972, Aerosil R805 (all manufactured by Nippon Aerosil Co., Ltd.), and the like.

When hydrophilic silicic acid anhydride is used as silicic acid anhydride, and the amount is about 10% by weight or more for the total weight of the pressure-sensitive adhesive layer, it is difficult to form an adhesive layer by ordinary methods such as the roll coater technique, blade technique, etc., because of an extremely high thixotropy index of adhesive material. Also, because the adhesive material that is obtained tends to become hygroscopic, the preparation is susceptible to being peeled from the skin surface when it is made to adhere thereto. The inventors have found that the combination of the hydrophilic silicic acid anhydride and the hydrophobic silicic acid anhydride can solve these problems. The amounts of the hydrophilic silicic acid anhydride, and the hydrophobic silicic acid anhydride that can be added are 20–80% by weight, and 80–20% by weight, respectively, based on the total weight of the silicic acid anhydride. If the amount of the hydrophobic silicic acid anhydride is less than 20% by weight, the coating properties of the adhesive material, and the adhesiveness of the pressure-sensitive adhesive layer cannot be improved sufficiently. If the amount of the hydrophobic silicic acid anhydride is more than 80% by weight, the silicic acid anhydride is less effective in improving the cohesive strength of the adhesive material.

As described above, the addition of the silicic acid anhydride to the adhesive material increases the cohesive strength and hardness of the pressure-sensitive adhesive layer with the decrease of its adhesiveness. However, since the viscosity of the pressure-sensitive adhesive layer in which the adhesive base material is compatible with nitroglycerin does not vary after the silicic acid anhydride is added, the rate of release of the nitroglycerin from the adhesive layer is not influenced by the addition of the silicic acid anhydride. Therefore, when the silicic acid anhydride is added, the cohesive strength and hardness of the pressure-sensitive layer are improved without causing a reduction in the rate of release of nitroglycerin.

Nitroglycerin is contained in the pressure-sensitive adhesive layer mentioned above in an amount of 10–30% by weight, and preferably 15–25% by weight. If the amount of nitroglycerin is less than 10% by weight, a sufficient release of the nitroglycerin is not attained. On the other hand, if the amount of nitroglycerin is more than 30% by weight, the nitroglycerin is not compatible with the (co)polymer contained in the adhesive layer, so that any excess amount of nitroglycerin will ooze out of the surface of the adhesive layer, which causes a reduction in its adhesiveness. According to the Fick's diffusion equation, the relationship between the concentration of a drug and the rate of release of the drug is expressed by a linear function. In the case of using nitroglycerin as a drug, when the amount of nitroglycerin is increased, the viscosity of the adhesive layer is reduced, so that the diffusion coefficient of nitroglycerin will become higher with the increase of the amount of nitroglycerin. Therefore, when a high concentration of nitroglycerin is contained in the adhesive layer, the rate of release of the nitroglycerin is increased in proportion to the increase of its diffusion coefficient, and it is increased at higher rate than that expressed by the linear function relationship. When the concentration of the nitroglycerin is increased further, the pressure-sensitive adhesive layer becomes softer with the decrease of its viscosity, so that an excellent adhesiveness with less mechanical skin irritation will be exhibited.

To the pressure-sensitive adhesive layer of the preparation of this invention, an alkyl ester of fatty acid is optionally added. The addition of the alkyl ester of fatty acid contributes to the increase of the diffusion coefficient of the nitroglycerin contained in the pressure-sensitive adhesive layer. Therefore, the rate of release of the nitroglycerin is significantly increased by adding the alkyl ester of fatty acid together with nitroglycerin to the adhesive base material. The alkyl ester of fatty acid that can be used includes an ester of fatty acid having about 22 or less carbon atoms and a monohydric or polyhydric alcohol having about 22 or less carbon atoms. These alkyl esters of fatty acid include, for example, an ester of neutral oil fatty acid, octyl laurate, isopropyl myristate, octyldodecyl myristate, butyl stearate, and the like. These alkyl esters of fatty acid are all oil based materials which are not likely to irritate the skin. When one or more of these esters are formulated in the pressure-sensitive adhesive layer containing the (co)polymer mentioned above, nitroglycerin, and the silicic acid anhydride, the esters are compatible with the mixed phase of the (co)polymer and the nitroglycerin to reduce its viscosity. In this way, the diffusion coefficient of nitroglycerin is increased significantly, so the release of the nitroglycerin from the pressure sensitive adhesive layer is increased. Consequently, a soft pressure-sensitive adhesive layer with excellent adhesiveness and less irritation can be obtained. The amount of the alkyl ester of fatty acid is usually 25% by weight or less, and preferably 5–15% by weight. If the amount of the alkyl ester of fatty acid is more than 25% by weight, the alkyl ester is not readily compatible with the adhesive layer.

Generally when acryl-type pressure-sensitive adhesive materials are used in percutaneous-administration-type pharmaceutical preparations, the following methods have been employed in order to ensure an appropriate cohesion: (1) a method for the manufacture of pressure-sensitive adhesive in which monomers having polar groups such as carboxyl groups, hydroxyl groups, amide groups, or the like are used as a component of the copolymer, and (2) a method in which the formed pressure-sensitive adhesive layer is cross-linked by the use of metal ions, urethane compounds, epoxy compounds, melamine compounds, peroxides, etc., or by irradiation of an electron beam. However, with the use of method (1) mentioned above, the affinity of the polar groups and the nitroglycerin is too great, so the skin-adhesive partition coefficient of nitroglycerin will decrease. Also, because the adhesive base material is not softened sufficiently by the addition of nitoroglycerin, the diffusion coefficient of nitroglycerin is not increased beyond a fixed value, so that the rate of release of the nitroglycerin will be low. With the use of method (2), nitroglycerin is decomposed during the crosslinking reaction, and the resulting crosslinked pressure-sensitive adhesive layer is not soft, thus the rate of release of the nitroglycerin is low as well as in method (1). On the other hand, in this invention, a (co)polymer having a specific composition is used, and the (co)polymer, nitroglycerin and the silicic acid anhydride are mixed together as described above, thereby exhibiting pressure-sensitive adhesiveness, and providing satisfactory cohesiveness. Therefore, the rate of release of the nitroglycerin is not decreased, different from the aforementioned conventional methods.

For use as the backing of the preparation of this invention, materials impermeable to drugs that are ordinarily used as the backings of the preparation can be used, and in particular, films and sheets having gas barrier properties can be used. As materials for the backing, there are, for example, polyester, polyamide, polyvinylidene chloride, polyvinyl chloride, aluminium, polyethylene, and polypropylene, and the like. It is also possible to use a laminated film which comprises a film or sheet made of above-mentioned substances and a film or sheet made of other substances such as polyethylene, polypropylene, ethylene-vinyl acetate copolymer, etc. For example polyethylene film; a laminated film of polyester film and ethylene-vinyl acetate copolymer film; and a laminated film of polyvinylidene chloride film and polyethylene film are preferred The surface area of the pressure-sensitive adhesive layer of the preparation is protected, where necessary, by release paper. As the release paper, a film made of, for example, polyester, polyvinyl chloride, polyvinylidene chloride, etc., can be used; it is possible to use laminated films made of high-quality paper or glassine paper and polyolefin film, etc. Ordinarily, so that the paper can be peeled off from the pressure-sensitive adhesive layer, the surface of the paper that comes into contact with the pressure-sensitive adhesive layer is treated with silicon.

The preparation of this invention can be manufactured by dissolving the (co)polymer mentioned above, nitroglycerin, and optionally, an alkyl ester of fatty acid into a suitable organic solvent, mixing a silicic acid anhydride with this solution, applying the mixture to the backing, and drying the coated layer on the backing. There is another method in which the mixture is applied to the release paper mentioned above and dried, and the pressure-sensitive adhesive layer thus obtained on the release paper is then affixed to the backing so that the adhesive layer is transferred to the surface of the backing. Nitroglycerin is contained in an amount of about 10-30% by weight in the pressure-sensitive adhesive layer, as described above, but because a few percent of nitroglycerin volatilize during the manufacturing process, it is preferable to formulate a slightly excess amount of nitroglycerin compared with that mentioned above at the time of manufacture. As the solvent to dissolve the (co)polymer and nitroglycerin, solvent systems with the solubility parameter of 8.9-9.9 can be used. As such solvents, there are toluene, methyl propionate, dichloroethane, dichloropropane, ethyl acetate, tetrahydrofuran, benzene, chloroform, methyl ethyl ketone, pentachloroethane, methyl acetate, trichloroethane, tetrachloroethane, dichloroethane, acetone, etc. Alternatively, it is possible to use a solvent mixture, with the proviso that the solvent mixture has a solubility parameter within the above limit. For example, cyclohexane which has a solubility parameter of 8.2, hexane which has a solubility parameter of 7.3, diethylether which has a solubility parameter of 7.4, or the like can be used as mixtures with another solvent having higher solubility parameter. In the above solvent system, the (co)polymer and the nitroglycerin can be dissolved uniformly. Also, when the preparation is being dried, it is possible to remove such a solvent system at a relatively low temperature over a relatively short period of time. Therefore, the amount of nitroglycerin that volatilizes can be minimized. If the solvent system has solubility parameters of less than 8.9, then the affinity of the solvent and the copolymer will be large, and thus a high temperature and a long period of time will be needed for the removal and drying of the solvent. For that reason, the amount of nitroglycerin that volatilizes increases, which is dangerous. On the other hand, in a polar solvent system with solubility parameters greater than 9.9, it is difficult to dissolve the (co)polymer uniformly.

The pressure-sensitive adhesive layer formed by the application of a mixture containing nitroglycerin, a (co)polymer, a silicic acid anhydride, and an alkyl ester of fatty acid is usually dried at a temperature of from room temperature to around 100° C., so as to minimize the amount of nitroglycerin that volatilizes from the pressure-sensitive adhesive layer.

Antiallergy agents, antioxidants, deodorants, etc., may be further added, if necessary, provided that the release of the nitroglycerin and the adhesiveness of the pressure-sensitive adhesive layer are not damaged.

So that the permacological effect of nitroglycerin via percutaneous absorption will be obtained continuously for, for example, a 24-hour period, 2.5–20 mg of nitroglycerin, and preferably about 10 mg of nitroglycerin per patient must be absorbed through the skin at a constant rate. So that the needed dose of nitroglycerin can be absorbed through the skin, the amount of nitroglycerin contained in the preparation of this invention should be about 5–40 mg, and ordinarily about 15 mg. In order that this amount of nitroglycerin will be contained, the thickness of the pressure-sensitive adhesive layer and the surface area of the preparation of this invention are determined as described below.

The thickness of the pressure-sensitive adhesive layer of the preparation of this invention is 30–200 $\mu$m, and preferably 60–150 $\mu$m. If the thickness of the pressure-sensitive adhesive layer is less than 30 $\mu$m, the adhesive strength is unsatisfactory, so that the preparation will readily come loose from the skin surface during use. Also, it is difficult to prepare a pressure-sensitive adhesive layer with a uniform thickness during manufacture. If the thickness of the pressure-sensitive adhesive layer is more than 200 $\mu$m, then a long period of time and a high temperature are needed to remove the solvent during manufacture. Therefore, a large amount of nitroglycerin will volatilize, giving rise to the danger of explosions. The surface area of the preparation depends on the concentration of nitroglycerin in the pressure-sensitive adhesive layer, the thickness of the pressure-sensitive adhesive layer, the intended dose of nitroglycerin, etc. In order to decrease the discomfort and the skin irritation caused by the adhesion of the preparation, it is preferable to use a preparation with small surface area. For that reason, the thickness of the pressure-sensitive adhesive layer is set at a relatively large value within the limits mentioned above, and nitroglycerin is contained in a high concentration uniformly. For example, when the thickness of the pressure-sensitive adhesive layer is set at 110 $\mu$m, and about 15 mg of nitroglycerin is contained in a concentration of 10%, then, the surface area of the preparation can be about 12 $cm^2$; and with a concentration of 30% for the nitroglycerin, the surface area of the preparation can be about 4 $cm^2$.

Since the alkyl (meth)acrylate (co)polymer that can be used in the preparation of this invention does not contain any polar group, the pressure-sensitive adhesive layer softens with the increase of the amount of nitroglycerin added, and the diffusion coefficient of nitroglycerin is higher. Thus the release of the nitroglycerin is increased. Therefore, the rate of release of the nitroglycerin is increased more rapidly than the increase of the concentration of the nitroglycerin contained in the pressure-sensitive adhesive layer.

Also, the silicic acid anhydride used in the preparation of this invention improves the cohesive strength of the pressure-sensitive adhesive layer without damaging the release of nitroglycerin. When the combination of a hydrophilic silicic acid anhydride and a hydrophobic silicic acid anhydride is employed, the adhesiveness of the resulting preparation to the skin surface will be improved. When the preparation is manufactured by the coating method using solvent, the coating properties of the mixture containing an adhesive material and silicic acid anhydride are improved. Thus, satisfactory cohesive strength of the pressure-sensitive adhesive layer can be obtained while maintaining a good release of nitroglycerin and suitable adhesiveness only when a specific alkyl (meth)acrylate and silicic acid anhydride are used.

Additionally, when an ester of fatty acid is added optionally, the rate of release of the nitroglycerin will be increased by softening the adhesive layer, ensuring its cohesive strength.

The adhesiveness of the pressure-sensitive adhesive layer in the preparation of this invention is relatively lower. However the adhesive layer is sufficiently soft, thus, the preparation sticks to the skin surface tightly, and it will not peel off easily. Also, because of the relatively weaker adhesiveness of the pressure-sensitive adhesive layer, the mechanical skin irritation, i.e., the separation of the horny substance, pulling the skin surface caused by the hair sticking to the adhesive layer, etc., is not likely to occur when the preparation is peeled off. The pressure-sensitive adhesive layer has good cohesive strength, so that the adhesive material does not remain on the skin surface when the preparation is peeled off.

In the preparation of this invention, it is not necessary to use any auxiliary absorbent such as surfactants since the diffusion coefficient of nitroglycerin contained in the pressure-sensitive adhesive layer is high. As a result, the preparation does not cause skin irritation. Also, because unreacted active groups and decomposed products of nitroglycerin are not present in the pressure-sensitive adhesive layer, a preparation which is much less irritating the skin can be obtained.

Furthermore, the concentration of nitroglycerin contained in the preparation of this invention have medium concentration of 10-30% by weight, so that it will be safer from the danger of explosion, compared to conventional preparations such as those disclosed in Japanese National Publications 61-502760 and 62-502965, which contain relatively higher concentrations of nitroglycerin, i.e., more than 30% by weight.

Finally, the preparation of nitroglycerin of this invention has only two layers i.e., the pressure-sensitive adhesive layer and backing, so it does not require complicated manufacturing processes. Therefore, it can be manufactured readily at low cost.

The following examples illustrate the present invention.

Example 1

(A) Manufacture of percutaneous-administration-type pharmaceutical preparation:

First, 2286 g of dodecyl methacrylate(DM), 14256 g of 2-ethylhexyl methacrylate(HM), 1656 g of 2-ethylhexyl acrylate(HA), 2.3 g of hexanediol dimethacrylate(NKHD), and 8500 g of ethyl acetate were charged into a 40-liter polymerization vessel, and heated to 80° C. Then, a solution of 16 g of lauroyl peroxide in 1500 g of cyclohexane was added to this reaction mixture over 6 hours, thereby proceeding the polymerization reaction. Thus, a solution of an alkyl (meth)acrylate copolymer having a weight average molecular weight of $1.05 \times 10^6$, and a solid content of 58% was obtained. The rolling ball tack value of the alkyl (meth)acrylate copolymer was 2 or less. In this specification, the rolling ball tack value of a (co)polymer was measured by the use of an adhesive tape prepared by forming an adhesive layer of the (co)polymer 80 μm in thickness on the polyester surface of a laminated film composed of polyester film and ethlene-vinyl acetate copolymer film.

The copolymer solution, a 10% ethyl acetate solution of nitroglycerin, hydrophilic silicic acid anhydride having an average primary particle size of 0.012 μm (NIPPON AEROSIL Co., Ltd.), and isopropyl myristate (IPM) were mixed in amounts so that the composition shown in Table 1 can be attained after the drying procedure described below. The mixture was stirred by a dissolver, and a solution containing about 30% of nonvolatile components was obtained. The solution was applied to the surface of a polyester release paper so that the thickness of the applied layer would be 100 μm after the drying procedure. The release paper with the applied layer was dried at 60° C. for 30 minutes to obtain a pressure-sensitive adhesive layer. A laminated film (i.e., backing) of 32 μm thick, composed of polyester film and ethylene-vinylacetate copolymer (EVA) film was applied to the surface of the pressure-sensitive adhesive layer so that the polyester film side came into contact with the adhesive layer, thus obtaining a percutaneous-administration-type pharmaceutical preparation of nitroglycerin.

(B) Evaluation of preparation:

The preparation obtained in item(A) was evaluated by a release experiment, and a holding strength experiment. The results are shown in Table 1, which also shows the results of Example 2 and Comparative Examples 1-3. The release experiment and holding strength experiment were carried out by the following procedure.

Release experiment:

The release experiment was conducted according to an experiment for in vitro percutaneous absorption of nitroglycerin through hairless mouse skin. The skin removed from the back of hairless mice was fixed on a Franz's diffusion cell. The preparation sample having 3.14 cm² area was applied to the upper side of the skin. Then, 24 hours later, the amount of nitroglycerin (mg/cm²) that was released into a receptor solution placed under the skin was measured by the HPLC procedure. The diffusion cell was maintained at 37° C., and a 20% aqueous solution of polyethylene glycol was used as the receptor solution. The release of nitroglycerin was estimated by determining a relative value, assuming that the amount of nitroglycerin released from the preparation of Comparative Example 1, i.e., 0.34 mg/cm², was 100%.

Holding strength experiment:

The holding strength of the preparation was measured according to the procedure of JIS Z-0237, Adhesive Tape and Adhesive Sheet Test Procedure. The preparation was cut to a 25 mm × 50 mm rectangular sample piece. The upper part (25 mm × 25 mm) of this sample piece was applied to a stainless steel plate. Then, a weight of 1 kg was loaded on the lower edge portion of the sample. The sample was allowed to stand in an oven at a temperature of 40° C. The holding strength was determined by measuring the periods of time until the sample was peeled from the stainless steel plate, and dropped.

Example 2

A percutaneous-administration-type pharmaceutical preparation was manufactured and evaluated by the same procedure as in Example 1 except that a polyethylene film having a thickness of 50 μm was used instead of the laminated film composed of polyester film and ethylene-vinylacetate copolymer film, and the composition shown in Table 1 was used for the adhesive layer.

Comparative Examples 1-3

Percutaneous-administration-type pharmaceutical preparations were manufactured and evaluated by the same procedure as in Example 1 except that the compositions shown in Table 1 were used for the adhesive layer.

TABLE 1

| | Composition of adhesive layer (% by weight) | | | | Release (%) | Holding strength (min.) |
|---|---|---|---|---|---|---|
| | Co-polymer | Nitro-glycerin | A-200[1] | Isopropyl myristate | | |
| Example 1 | 67.6 | 15.5 | 10.1 | 6.8 | 182 | >60 |
| Example 2 | 59.1 | 20.9 | 12 | 8 | 221 | 27 |
| Comparative Example 1 | 85 | 15 | — | — | 100 | 13 |
| Comparative Example 2 | 77.1 | 15.4 | — | 7.5 | 186 | 0.3 |
| Comparative Example 3 | 76.4 | 23.6 | — | — | 227 | 0 |

[1] Hydrophilic silicic acid anhydride (NIPPON AEROSIL CO., Ltd.: AEROSIL 200)

It can be seen from Table 1 that the preparation of Example 1 containing the hydrophilic silicic acid anhydride (A-200) and isopropyl myristate (IPM) exhibits excellent release of nitoroglycerin and holding strength. The preparation of Example 2 containing a high concentration of nitroglycerin has the improved release of nitroglycerin without causing the reduction of the holding strength. On the other hand, the preparation of Comparative Example 1 that does not contain both hydrophilic silicic acid anhydride (A-200) and isopropyl myristate (IPM) has apparently poorer release and holding strength values. Although the preparation of Comparative Example 2, containing only IPM, and not containing hydrophilic silicic acid anhydride (A-200), exhibits excellent release of nitroglycerin, it has lower holding strength. Also, when it is peeled from the skin surface, the adhesive material will remain on the skin surface because of a lower cohesive strength of the pressure-sensitive adhesive layer. The preparation of Comparative Example 3 that contains a high concentration of nitroglycerin and does not contain either hydrophilic silicic acid anhydride (A-200) or isopropyl myristate (IPM) has improved release of nitroglycerin, but the holding strength is low.

Example 3

Using the preparation which was manufactured in Example 2, a transferability experiment was carried out by the following procedure.

Transferability experiment:

The preparation was cut to a 1.5 cm×1.5 cm sample. The sample was applied to the chests of human subjects for 24 hours. The amount of nitroglycerin transferred by percutaneous administration was calculated by the difference between the amounts of nitroglycerin contained in the preparation before and after 24 hour-application. The results are shown in Table 2, which also shows the results of Comparative Example 4 described below.

Comparative Example 4

The procedure of Example 3 was followed except that the preparation which was manufactured in Comparative Example 1 was used.

TABLE 2

| | Amount of nitroglycerin transferred (mg/cm$^2$) |
|---|---|
| Example 3 | 0.41 |
| Comparative Example 4 | 0.20 |

Reference Example

Study for a suitable amount of silicic acid anhydride

Using the copolymer of Example 1, various percutaneous-administration-type pharmaceutical preparations were manufactured by varying the amount of silicic acid anhydride (A-200) as shown in Table 3. These preparations were evaluated by the same holding strength experiment as in Example 1. Also, the SP adhesive strength of the preparations was measured by the following 180 degree peeling test.

SP adhesive strength (180 degree peeling test):

This test was carried out according to the procedure of JIS Z-0237, Test Procedure for Adhesive Tape and Adhesive Sheet. The preparation was cut into a sample strip 15 mm in width and 100 mm or more in length. The sample strip was applied to a stainless steel plate, and pressed by a 1 kg load. Then, the sample strip was peeled off from the stainless steel plate, by folding one of the edges of the strip and pulling this folded portion along the length of the strip. The amount of load required for pulling the strip at the rate of 300 mm/minute was measured. The load (g/15 mm) was expressed by a SP (Strength of Peel) adhesive strength.

Table 3 shows the results of the experiments mentioned above.

TABLE 3

| | Composition of adhesive layer (% by weight) | | | | Holding strength (min.) | SP adhesive strength (g/15 mm) |
|---|---|---|---|---|---|---|
| | Co-polymer | Nitro-glycerin | A-200 | Isopropyl myristate | | |
| Sample 1 | 64 | 23 | 3 | 10 | 0 | >800 |
| Sample 2 | 60 | 23 | 7 | 10 | 8 | 620 |
| Sample 3 | 57 | 23 | 10 | 10 | 16 | 540 |
| Sample 4 | 52 | 23 | 15 | 10 | >60 | 165 |
| Sample 5 | 52 | 23 | 17 | 8 | >60 | 5 (Slightly adhesive) |
| Sample 6 | 47 | 23 | 22 | 8 | >60 | 0.5 (Not adhesive) |
| Sample 7 | 42 | 23 | 27 | 8 | Impossible to form adhesive layer | |

As shown in Table 3, when the amount of the silicic acid anhydride is less than 5% by weight, the preparation does not have sufficient holding strength. On the other hand, when the amount of the silicic acid anhydride is more than 20% by weight, the SP adhesive strength of the preparation is decreased, significantly. Therefore, the suitable amount of the silicic acid anhydride is in the range of 5–20% by weight.

Examples 4–7

Using the composition shown in Table 4, a percutaneous-administration-type pharmaceutical preparation was manufactured by the same procedure as in Example 1 except that a laminated film 45 μm in thickness composed of polyethylene film, polyvinylidene chloride film, and polyethylene film was used instead of the laminated polyester/EVA film. The preparation was evaluated as in Example 1. Furthermore the coating properties during the formation of the adhesive layer in the manufacture of the preparation, and the application properties of the preparation were evaluated as follows.

Coating properties:

The coating properties were evaluated by determining whether the adhesive layer can be formed continuously with a given thickness by the use of a roll coater or blade coater.

O: A continuous smooth coating can be carried out.

Δ: A continuous coating can be carried out for a short period of time.

X: A continuous coating is difficult to be carried out.

Application properties:

The preparation was cut into a 1.5 cm×1.5 cm sample piece. The sample was applied to the chests of human subjects, and 24 hours later, it was observed whether the sample piece was peeled or not. Also, after the sample piece was peeled off, the skin surface was observed to see if any adhesive material was left or not. The results were shown as the ratio of the number of the subjects in which "no peeling", "partial peeling", and "remaining of the adhesive material" were observed to the total number of the subjects.

Table 4 shows the results of these experiments. In Table 4 and other tables of this specification, R-972 denotes AEROSIL R 972 (Nippon Aerosil Co. Ltd.) which is a hydrophobic silicic acid anhydride having an average primary particle size of about 0.016 μm.

procedure of Example 1, and the amount of nitroglycerin that was transferred into the receptor solution placed under the skin after a fixed period of time shown in Table 6 from the beginning of the application was shown as the amount of released nitroglycerin per unit of area (mg/cm$^2$). The irritation experiment was carried out as follows.

Irritation experiment:

The preparations were applied to the backs of six domestic white rabbits, the hair of the backs of which was previously removed. After the applied preparations were allowed to stand for 24 hours, they were peeled off, and the appearance of red spots and edemata on the surface of the backs was observed. The irritation was estimated according to a Draze's procedure, and indicated by a primary irritation index (PII). The irritation of a substance is classified into the groups as shown in Table 5.

TABLE 5

| Safety classification | Primary irritation Index |
| --- | --- |
| Weak Irritating Substance | 0–2 |
| Medium Irritating Substance | 3–5 |
| Strong Irritating Substance | 6< |

Comparative Example 5

TABLE 4

| | Composition of adhesive Layer (% by weight) | | | | | Release (%) | Holding strength (min.) | Coating properties | Application properties | | |
| --- | --- | --- | --- | --- | --- | --- | --- | --- | --- | --- | --- |
| | Copolymer | Nitro-glycerin | A-200 | R-972 | Isopropyl myristate | | | | No peeling | Partial peeling | Remaining of adhesive material |
| Example 4 | 54.8 | 23.2 | 14 | — | | 214 | >60 | X | 2/4 | 2/4 | 0/4 |
| Example 5 | 53.2 | 24.8 | 7 | 7 | 8 | 292 | 12 | O | 4/4 | 0/4 | 0/4 |
| Example 6 | 54 | 23 | 4 | 10 | 8 | 228 | 6 | O | 4/4 | 0/4 | 0/4 |
| Example 7 | 67.6 | 15.5 | — | 10.1 | 6.8 | 153 | 11 | O | 4/4 | 0/4 | ¼ |

It is apparent from Table 4 that the use of the hydrophobic silicic acid anhydride (AEROSIL R972) can improve the coating properties of the adhesive layer, while maintaining the holding strength and release of nitroglcerin from the preparation. Moreover, less peelings were observed, and therefore it can be seen that the application properties of the preparation were improved.

Example 8

Using the composition shown in Table 6, a percutaneous-administration-type pharmaceutical preparation was manufactured by the same procedure as in Example 1 except that the thickness of the adhesive layer was adjusted to 150 μm. The resulting preparation was evaluated by a release experiment and irritation experiment. The results are shown in Table 6, which also shows the results of Comparative Example 5 described below. The release experiment was carried out according to the Commercially available percutaneous-administration-type pharmaceutical preparation in tape form which achieves the highest release of nitroglycerin per area, MINITRAN (manufactured by 3M Riker Co., Ltd.) was evaluated by the same procedure as in Example 5.

This preparation is composed of a polyethylene film, and an adhesive layer formed on one side of the polyethylene film. The adhesive layer contains the following composition:

Drug: About 30% by weight of nitroglycerin based on the total weight of the adhesive layer.

Adhesive base material: About 96% by weight of isooctyl acrylate-acryl amide copolymer, about 2% by weight of ethyl oleate, and 2% by weight or less of glycerin monolaurate.

The percutaneous absorption rate of nitroglycerin contained in the preparation through the human skin is 5 mg/24 hr./6.7 cm$^2$.

TABLE 6

| | Composition of adhesive Layer (% by weight) | | | | | Nitroglycerin content (mg/cm$^2$) | Release | | Irritation (PII) |
| --- | --- | --- | --- | --- | --- | --- | --- | --- | --- |
| | Copolymer | Nitro-glycerin | A-200 | R-972 | Isopropyl myristate | | Release time (hr.) | Released Nitroglycerin (mg/cm$^2$) | |
| Example 8 | 52.7 | 25.3 | 7 | 7 | 8 | 3.80 | 6 | 0.37 | 0.9 |
| | | | | | | | 20 | 1.23 | |
| | | | | | | | 24 | 1.43 | |
| Comparative Example 5 | Commercially available preparation MINITRAN | | | | | 2.69 | 5 | 0.14 | 1.6 |
| | | | | | | | 20 | 0.75 | |

TABLE 6-continued

| Composition of adhesive Layer (% by weight) | | | | | Nitroglycerin content (mg/cm$^2$) | Release time (hr.) | Released Nitroglycerin (mg/cm$^2$) | Irritation (PII) |
|---|---|---|---|---|---|---|---|---|
| Copolymer | Nitroglycerin | A-200 | R-972 | Isopropyl myristate | | 24 | 0.90 | |

It is apparent from Table 6 that the preparation of this invention exhibits much higher release of nitroglycerin and less irritation than the commercially available preparation which has the highest release ability of nitroglycerin per area.

Comparative Example 6

A copolymer solution having a composition similar to commercially available adhesives was prepared by the following procedure. First, 170 g of 2-ethylhexyl acrylate (HA), 20 g of vinyl acetate (VAc), 10 g of acrylic acid (AA), 112 g of hexane, and 24 g of toluene were charged into a 1 liter glass vessel equipped with a stirrer, and heated to 70° C. under a nitrogen atmosphere. Then, a solution of 2.4 g of lauroyl peroxide in 50 g of hexane was added dropwise over an hour, thereby proceeding the polymerization reaction for additional 7 hours. After the polymerization reaction was completed, a copolymer solution having a solid content of 46.4%, and a viscosity of 16400 cps was obtained by adding 50 ml of hexane to the mixture.

Using the copolymer solution together with the compositions shown in Table 7, a percutaneous-administration-type pharmaceutical preparation was manufactured and evaluated for its holding strength by the same procedure as in Example 1. The results are shown in Table 7, which also shows the results of Example 5 described above, and Comparative Example 7 described below.

Comparative Example 7

The adhesive material described in Japanese laid-Open Patent Publication 57-77617 was prepared by the following procedure. First, 172 g of dodecyl methacrylate (DM), 20 g of vinyl acetate (VAc), 8 g of acrylic acid (AA), 112 g of hexane, and 24 g of toluene were charged into a 1 liter glass vessel equipped with a stirrer, and heated to 70° C. under nitrogen atmosphere. Then, a solution of 2.4 g of lauroyl peroxide in 50 g of toluene was added dropwise over an hour, thereby proceeding the polymerization reaction for additional 7 hours. After the polymerization reaction was compeleted, a copolymer solution having a solid content of 39.2%, and a viscosity of 66400 cps was obtained by adding 114 ml of hexane to the mixture.

Using the copolymer solution, a percutaneous-administration-type pharmaceutical prepatration was manufactured and evaluated in its holding strength by the same procedure as in Example 1.

TABLE 7

| | Copolymer components (Weight ratio) | Composition of adhesive layer (% by weight) | | | | | Holding strength (min.) |
|---|---|---|---|---|---|---|---|
| | | Copolymer | Nitroglycerin | A-200 | R-972 | Isopropyl myristate | |
| Example 5 | DM/HM/HA (12.6:78.3:9.1) | 53.2 | 24.8 | 7 | 7 | 8 | 12 |
| Comparative Example 6 | HA/VAc/AA (85:10:5) | 58 | 20 | 7 | 7 | 8 | 1 or less |
| Comparative Example 7 | DM/VAc/AA (86:10:4) | 58 | 20 | 7 | 7 | 8 | 1 or less |

It can be seen from Table 7 that when a high concentration of nitroglycerin is contained in the adhesive material having a similar composition to commercially available adhesive materials (Comparative Example 6), or in the adhesive material described in Japanese Laid-Open Patent Publication 57-77617 (Comparative Example 7) with the addition of silicic acid anhydride, the holding strength of the resulting preparation is not improved because the cohesive strength of the adhesive material is not increased. On the other hand, the specific adhesive material described in Example 5 was used, the preparation exhibits good cohesive strength even when a high concentration of nitroglycerin is contained therein.

Example 9

Copolymer components of 100 g of 2-ethylhexyl methacrylate (HM), 100 g of 2-ethylhexyl acrylate (HA), and 0.025 g of hexanediol dimethacrylate were added to 136 g of ethyl acetate, and heated to 60° C. Then, 10 g of 6% hexane solution of lauroyl peroxide were added to the mixture in portions, thereby proceeding the polymerization reaction for 10 hours, resulting in a copolymer solution. The copolymer solution had a solid content of 61%, a viscosity of 380,000 cps, and a rolling ball tack value of the copolymer was 2 or less. Using the copolymer solution, and the compositions shown in Table 8, a percutaneous-administration-type pharmaceutical preparation was manufactured and evaluated in its release of nitroglycerin by the same procedure as in Example 1. The results are shown in Table 8, which also shows the results of Comparative Example 8 described below.

Comparative Example 8

A copolymer solution was prepared by the same procedure as in Example 9 except that 70 g of butyl acrylate (BA), and 130 g of 2-ethylhexyl acrylate (HA) were used as copolymer components. The copolymer solution had a solid content of 59%, and a viscosity of 350,000 cps. Using this copolymer solution, a percutaneous-administration-type pharmaceutical preparation was manufactured by the same procedure as in Example 9, and evaluated in its release of nitroglycerin by the same procedure as in Example 1.

TABLE 8

| Copolymer | Composition of adhesive layer (% by weight) | | | | Release[1] (mg/cm²) |
|---|---|---|---|---|---|
| | components (Weight ratio) | Co-polymer | Nitro-glycerin | A-200 | R-972 | |

| | components (Weight ratio) | Co-polymer | Nitro-glycerin | A-200 | R-972 | Release[1] (mg/cm²) |
|---|---|---|---|---|---|---|
| Example 9 | HM/HA (50:50) | 70 | 20 | 5 | 5 | 0.344 |
| Comparative Example 8 | BA/HA (35:65) | 70 | 20 | 5 | 5 | 0.138 |

[1] The amount of released nitroglycerin

It is apparent from Table 8 that a preparation of Comparative Example 8 which was manufactured by the use of butyl acrylate having an alkyl group of 4 carbon atoms as one of copolymer components allowed less release of nitroglycerin, compared to the preparation of this invention.

Example 10

Using the copolymer solution of Example 1, and the composition shown in Table 9, a percutaneous-administration-type pharmaceutical preparation was manufactured according to the procedure of Example 1. The rolling ball tack value of the copolymer contained in the pressure-sensitive adhesive layer of this preparation was 2 or less. The application properties of the preparation were evaluated by the same procedure as in Example 4. The results are shown in Table 9, which also shows the results of Comparative Examples 9 and 10 described below.

Comparative Example 9

A copolymer solution was prepared by the same procedure as in Example 9 except that 136.8 g of 2-ethylhexyl acrylate (HA), and 63.2 g of 2-ethylhexyl methacrylate were used as copolymer components. The copolymer solution had a solid content of 61%, and a viscosity of 390,000 cps. Using this copolymer solution, a percutaneous-administration-type pharmaceutical preparation was manufactured by the same procedure as in Example 10. The rolling ball tack value of the copolymer contained in the pressure-sensitive adhesive layer of this preparation was 32 or more. The application properties of the preparation were evaluated by the same procedure as in Example 4. The results were shown in Table 9.

Comparative Example 10

A copolymer comprising 45% by weight of dodecyl methacrylate, 35% by weight of 2-ethylhexyl methacrylate, and 20% by weight of 2-ethylhexyl acrylate was prepared according to the procedure of Example 1. The copolymer had a weight average molecular weight of about 1,600,000. The rolling ball tack value of this copolymer was 23. Using the copolymer, a percutaneous-administration-type pharmaceutical preparation containing 22% of nitroglycerin was manufactured according to the procedure of Example 11 below. Table 9 shows the results of the evaluation.

TABLE 9

| | Copolymer components (Weight ratio) | Composition of adhesive layer (% by weight) | | | | | Rolling ball tack value of copolymer | Application properties | | |
|---|---|---|---|---|---|---|---|---|---|---|
| | | Co-polymer | Nitro-glycerin | A-200 | R-972 | Isopropyl myristate | | No peeling | Partial peeling | Remaining of adhesive material |
| Example 10 | HA/HM/DM (9.1:78.3:12.6) | 60 | 20 | 6 | 6 | 8 | <2 | 5/5 | 0/5 | 0/5 |
| Comparative Example 9 | HA/HM (68.4:31.6) | 60 | 20 | 6 | 6 | 8 | >32 | 5/5 | 0/5 | 5/5 |
| Comparative Example 10 | HA/HM/DM (20:35:45) | 56 | 22 | 8 | 8 | 6 | 23 | 5/5 | 0/5 | 5/5 |

It can be seen from Table 9 that the preparation of Comparative Example 9 or 10 having a copolymer with rolling ball tack value of more than 2 has poorer application properties compared to the preparations of this invention. When the preparation of Comparative Example 9 or 10 was peeled off from the skin surface, the adhesive material remained on the surface of the skin because of the weak cohesive strength of the adhesive material.

Example 11

A percutaneous-administration-type pharmaceutical preparation was manufactured by the same procedure as in Example 1 except that the following composition was used for the adhesive layer, that the thickness of the pressure-sensitive adhesive layer was 110 μm, and that a polyethylene film having a 50 μm thickness was used as the backing.

| Composition used for adhesive layer (% by weight) | |
|---|---|
| Copolymer | 56 |
| Nitroglycerin | 22 |
| A-200 | 8 |
| R-972 | 8 |
| Isopropyl myristate | 6 |

The results of the evaluation of the preparation and the coating properties during the formation of the adhesive layer in the manufacture of the preparation are shown in Table 10 below. Among the items of the evaluation, the irritation test was carried out as follows.

Irritation test:

Samples of the preparation (1 cm × 1 cm) were applied to the chests or the inner area of the upper arms of 10 human subjects for 24 hours. After the samples were peeled off, the degree of erythema, eschar and edema on the skin surface was observed, and evaluated by the scores shown below. An irritation index was calculated by dividing the sum of the scores by the total number (i.e., 10) of the subjects.

| Degree of erythema, eschar, and Edema | Scores |
|---|---|
| None | 0 |
| Appreciable | 1 |
| Clearly noticeable | 2 |
| Very clearly noticeable | 3 |

TABLE 10

| Coating properties | ○ |
|---|---|
| Release (%) | 326 |
| Holding strength (minutes) | 33 |

TABLE 10-continued

| | |
|---|---|
| Amount of nitroglycerin transferred (mg/cm$^2$) | 0.652 |
| Application properties: | |
| No peeling | 5/5 |
| Partial peeling | 0/5 |
| Remaining of adhesive material | 0/5 |
| Irritation | 0 |
| SP adhesive strength (g/15 mm) | 198 |

Example 12

A copolymer comprising 5% by weight of dodecyl methacrylate, 5by weight of 2-ethylhexyl acrylate, and 90% by weight of 2-ethylhexyl methacrylate was prepared according to the procedure of Example 1. The copolymer had a weight average molecular weight of about 1,700,000. By the use of this copolymer, a percutaneous-administration-type pharmaceutical preparation of nitroglycerin was manufactured according to the procedure of Example 11. Release of nitroglycerin and the application properties of this preparation were evaluated. The results of the evaluation are shown in Table 11 along with the results of Example 13 below.

Example 13

A homopolymer was prepared by the use of 2-ethylhexyl methacrylate according to the procedure of Example 1. The polymer had a weight average molecular weight of about 1,750,000. By the use of this polymer, a percutaneous-administration-type pharmaceutical preparation of nitroglycerin was manufactured according to the procedure of Example 11. Release of nitroglycerin and the application properties of this preparation were evaluated. The results of the evaluation are shown in Table 11.

TABLE 11

| | | Application properties | | |
|---|---|---|---|---|
| | Release (%) | No peeling | Partial peeling | Remaining of adhesive material |
| Example 12 | 306 | 5/5 | 0/5 | 0/5 |
| Example 13 | 258 | 5/5 | 0/5 | 0/5 |

Table 11 shows that a homopolymer prepared from 2-ethylhexyl methacrylate or a copolymer having 2-ethylhexyl methacrylate in a high content is relatively hard. Thus, the release of nitroglycerin of the preparation that contains the (co)polymer is slightly low. However, the application properties of the preparation are satisfactory.

According to the present invention, a percutaneous-administration-type pharmaceutical preparation of nitroglycerin comprising a pressure-sensitive adhesive layer, wherein the pressure-sensitive adhesive layer contains nitroglycerin as a drug, and the effect of the nitroglycerin is sustained for at least 24 hours and the method for the manufacture of the preparation are provided. Since a specific alkyl (meth)acrylate (co)polymer is used as an adhesive base material in the preparation of nitroglycerin of this invention, the preparation exhibits a high degree of release of nitroglycerin due to the plasticization effect of the nitroglycerin. Therefore, a high concentration of nitroglycerin is not required for the preparation, and it is safe from the danger of explosion. Also, even a compact preparation can supply a sufficient amount of nitroglycerin. Moreover, because the preparation contains a silicic acid anhydride, and if desired, an alkyl ester of fatty acid, it has extremely lower skin irritation, and excellent application properties. Since the preparation of this invention has only a two-layer structure of a pressure-sensitive adhesive layer and a backing, it can be manufactured at low cost without any complicated processes.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A preparation of the percutaneous administration of nitroglycerin comprising a backing impervious to nitroglycerine and a pressure-sensitive adhesive layer placed on one surface of the backing, said pressure-sensitive adhesive layer containing 35-85% by weight of an alkyl (meth)acrylate (co)polymer comprising 40-100% by weight of 2-ethylhexyl methacrylate, 10-30% by weight of nitroglycerin and 5-20% by weight of a silicic acid anhydride as a cohesive strength improver.

2. A preparation according to claim 1, wherein the copolymer comprises 40-90% by weight of 2-ethylhexyl methacrylate.

3. A preparation according to claim 1, wherein the (co)polymer has a rolling ball tack value of 2 or less.

4. A preparation according to claim 1, wherein the pressure-sensitive adhesive layer contains 25% by weight or less of an alkyl ester of fatty acid.

5. A preparation according to claim 1, wherein the silicic acid anhydride comprises 20-80% by weight of a hydrophobic silicic acid anhydride and 80-20% by weight of a hydrophilic silicic acid anhydride.

* * * * *

UNITED STATES PATENT AND TRADEMARK OFFICE
CERTIFICATE OF CORRECTION

PATENT NO. : 5,260,064
DATED : November 9, 1993
INVENTOR(S) : Takashi Nakagawa, et. al.

It is certified that error appears in the above-indentified patent and that said Letters Patent is hereby corrected as shown below:

In Table 4, Columns 15/16, change:

TABLE 4

| | Composition of adhesive Layer (% by weight) | | | | Release (%) | Holding strength (min.) | Coating properties | Application properties | | |
|---|---|---|---|---|---|---|---|---|---|---|
| | Copolymer | Nitro-glycerin | A-200 | R-972 | Isopropyl myristate | | | | No peeling | Partial peeling | Remaining of adhesive material |
| Example 4 | 54.8 | 23.2 | 14 | — | | 214 | >60 | X | 2/4 | 2/4 | 0/4 |
| Example 5 | 53.2 | 24.8 | 7 | 7 | 8 | 292 | 12 | O | 4/4 | 0/4 | 0/4 |
| Example 6 | 54 | 23 | 4 | 10 | 8 | 228 | 6 | O | 4/4 | 0/4 | 0/4 |
| Example 7 | 67.6 | 15.5 | — | 10.1 | 6.8 | 153 | 11 | O | 4/4 | 0/4 | 1 |

UNITED STATES PATENT AND TRADEMARK OFFICE
CERTIFICATE OF CORRECTION

PATENT NO. : 5,260,064
DATED : November 9, 1993
INVENTOR(S) : Takashi Nakagawa, et. al.

It is certified that error appears in the above-indentified patent and that said Letters Patent is hereby corrected as shown below:

To:

Table 4

|  | Composition of adhesive Layer (% by weight) | | | | | Release (%) | Holding strength (min.) | Coating properties | Application properties | | |
|---|---|---|---|---|---|---|---|---|---|---|---|
|  | Co-polymer | Nitro-glycerin | A-200 | R-972 | Isopropyl myristate | | | | No peeling | Partial peeling | Remaining of adhesive material |
| Example 4 | 54.8 | 23.2 | 14 | — | 8 | 214 | >60 | × | 2/4 | 2/4 | 0/4 |
| Example 5 | 53.2 | 24.8 | 7 | 7 | 8 | 292 | 12 | ○ | 4/4 | 0/4 | 0/4 |
| Example 6 | 54 | 23 | 4 | 10 | 8 | 228 | 6 | ○ | 4/4 | 0/4 | 0/4 |
| Example 7 | 67.6 | 15.5 | — | 10.1 | 6.8 | 153 | 11 | ○ | 4/4 | 0/4 | 1/4 |

Signed and Sealed this

Thirtieth Day of August, 1994

Attest:

BRUCE LEHMAN

Attesting Officer

Commissioner of Patents and Trademarks